United States Patent [19]

van Staaveren

[11] Plant 4,635

[45] Jan. 27, 1981

[54] ALSTROEMERIA NAMED RED SUNSET

[76] Inventor: M. C. van Staaveren, 30, Hornweg, 1432 GM Aalsmeer, Netherlands

[21] Appl. No.: 32,678

[22] Filed: Apr. 23, 1979

[51] Int. Cl.[3] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—Chas. W. Rummler

[57] ABSTRACT

A new Alstroemeria variety characterized by its darkish red petals, the inner ones of which have a yellow base over which short brown pencil-stripe spots appear in longitudinally extending rows, and by its vigorous upright growth with more-or-less continuous production of flowers on each branch during each of its recurrent blooming seasons.

1 Drawing Figure

BACKGROUND OF THE INVENTION

This new Alstroemeria cultivar originated as a sport of an unnamed and unpatented variety selected from my breeding stock at Aalsmeer, Holland, and which had been subjected to Roentgen radiation at the I.T.A.L. Institute at Wageningen, Holland, in 1973. The parent variety is identified in my records as WC 1172 and the object of the radiation technique was to improve the color of WC 1172. This sport appeared to have accomplished my purpose and my asexual propagation of this new plant, at Aalsmeer, Holland, through successive generations, by dividing root stocks, has demonstrated that its distinctive characteristics hold true from generation to generation and appear to be firmly fixed. Propagation of this new variety is now being carried on at Aalsmeer, Holland, by dividing root stocks.

DESCRIPTION OF THE DRAWING

My new variety of Alstroemeria plant is illustrated by the accompanying photographic drawing which is a black and white rendition of the plant in full bloom, the drawing having been hand painted in part to show the true coloring and the form of the individual flowers.

DESCRIPTION OF THE NEW PLANT

The following is a detailed description of my new Alstroemeria cultivar with color designations according to The R.H.S. Colour Chart of The Royal Horticultural Society of London, England.

THE PLANT

Origin: Sport.

Parentage: An unnamed, unpatented variety identified in my records as WC 1172.

Classification:

*Botanic.*—Alstroemeria.

*Commercial.*—Hybrid Alstroemeria.

Form: Herb; a tall, slender flowering stalk with flower bearing branches in simple umbel arrangement at its top.

Height: About 1.30 to 1.70 meters.

Growth: Vigorous and upright.

Root stock: Tuberous; tubers bear 40 or more buds during the year from which the flower stalks grow in various stages of development during the course of the year.

Branching: Each flower stalk branches at the top into 4 to 7 flower bearing stems.

Foliage: Quantity — less than normal with 20 to 30 leaves.

*Leaf shape.*—Long and narrow, generally linear with acuminate tip.

*Texture.*—Soft.

*Color.*—Middle green.

THE BUD

Form: The young bud is pear-shaped and becomes long and pointed just before opening.

Opening rate: The bud opens slowly.

Peduncle: The length is variable growing outward from about 12 cm.

THE FLOWER

Blooming habit: Recurrent in early Spring and in Fall with profuse and more-or-less continuous blossoming during each blooming season.

Flower size: Medium.

*Diameter.*—About 4.5 cm.

*Depth.*—About 4 cm.

Shape: Generally funnel-like.

Borne: Singly on a long peduncle or stem.

Petalage: Number of petals — 6.

*Arrangement.*—Two concentric circles of 3 petals each.

*Form.*—Wide, elliptic and slightly serrated at its outer end.

*Color.*—Outer petals — 41B to 44C. Inside petals — body, 41B to 44C; base, 9A at opening, becoming 12A as the flower matures.

Discoloration after full bloom: As the flower matures, the color becomes a combination of 47C and 48B.

Persistence: The flowers hang on and dry.

Peduncle: Sturdy and upright, the length depending upon age in the blooming season.

Lasting quality:

*On the plant.*—10 days for each flower.

*As a cut flower.*—At least 7 days for each flower.

REPRODUCTIVE ORGANS

Stamens:

*Number.*—One opposite each petal.

*Anthers.*—Length — about 6 to 8 mm.

*Filaments.*—Length — about 4 cm. Color: Orange-Red.

Pistils: Number — only one.

*Length.*—About 3 cm.

This new variety of Alstroemeria plant is particularly distinguished by the red and yellow coloration of its blooms and the straight, sturdy and upright peduncle for each of the flowers.

I claim:

1. The new and distinct variety of Alstroemeria plant substantially as herein shown and described, characterized by the distinctive red coloring of the flowers and the yellow coloring at the base of each of the inside petals, and by the straight, sturdy and long peduncle which supports each of the flowers.

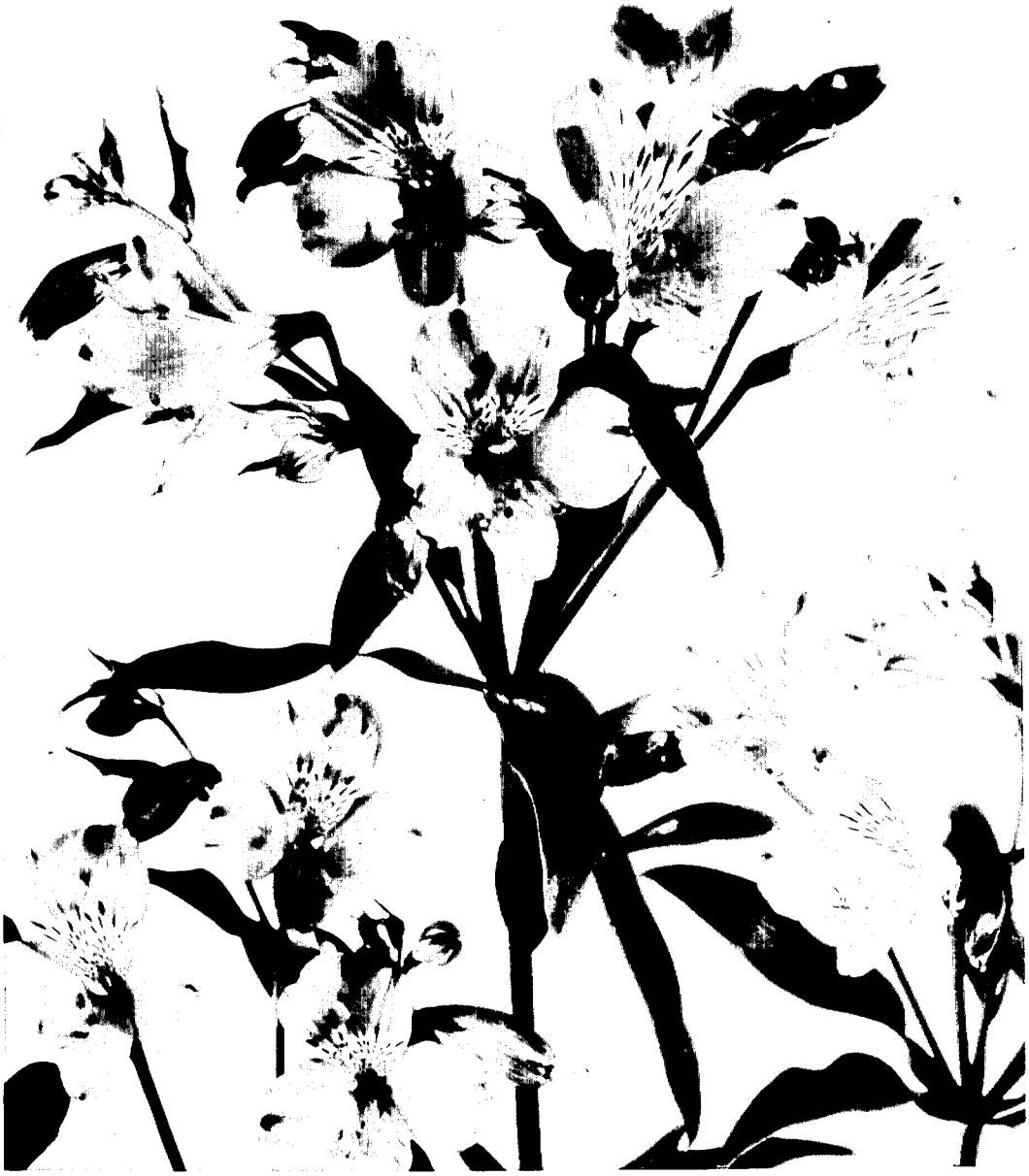

* * * * *